United States Patent [19]

Mumme et al.

[11] Patent Number: 5,486,177
[45] Date of Patent: Jan. 23, 1996

[54] PATELLA PLANER WITH ADJUSTABLE STOP

[75] Inventors: Charles W. Mumme; Philip Gold, both of Austin, Tex.

[73] Assignee: Intermedics Orthopedics, Inc., Austin, Tex.

[21] Appl. No.: 359,873

[22] Filed: Dec. 20, 1994

[51] Int. Cl.[6] ................................. A61B 17/17
[52] U.S. Cl. ................ 606/79; 606/88; 606/172; 408/241.S; 408/115 R
[58] Field of Search ................ 606/79, 80, 86, 606/87, 88, 96, 172; 81/347, 352–356; 269/6, 157, 215; 408/115 R, 115 A, 108, 241 S

[56] References Cited

U.S. PATENT DOCUMENTS

| | | | |
|---|---|---|---|
| 4,567,886 | 2/1986 | Peterson | 606/88 |
| 5,284,482 | 2/1994 | Mikhail | 606/86 |
| 5,342,364 | 8/1994 | Mikhail | 606/86 |

*Primary Examiner*—Tamara L. Graysay
*Attorney, Agent, or Firm*—John R. Merkling

[57] ABSTRACT

A patella planer for preparing a resected surface on a patella in a single operation. The patella planer has an adjustable stop which can be used on either side of the planer so that the planer may be used on the right or left knee. The adjustable stop has a floating zero pointer which can be set to accommodate varying thickness of the patient's patella. The amount of patella material to be removed can be selected by adjusting an offset stop pin.

14 Claims, 4 Drawing Sheets

PATELLA PLANER WITH ADJUSTABLE STOP

FIELD OF OUR INVENTION

Our invention relates to apparatus for surgery, and particularly for orthopedic surgery related to the knee, and most specifically to apparatus for preparing the patella to receive an artificial surface which would cooperate with a implanted prosthetic knee having femoral and tibial components.

BACKGROUND OF OUR INVENTION

Orthopedic prosthetic knees are available from many manufacturers, including Intermedics Orthopedics, Inc., the assignee of our present invention. Such prosthetic knees typically comprise a tibial component and a femoral component. The tibial component replaces the condyle compartments on the proximal end of a patient's tibia. The femoral component replaces the distal end of the patient's femur and provides artificial condyles which articulate with the condyle compartments of the prosthetic tibial component. In addition, it is frequently necessary to provide an additional artificial surface on the patella. The patella rides between the condyles of the knee and provides an attachment point for various tenons. Because of the numerous tenons attached to the knee and its importance in controlling the mechanics of the knee, it is usually inadvisable to remove the patella entirely. However, it may be necessary to provide a new articulating surface adjacent the artificial condyles of the knee prosthesis. A prosthetic patella surface has been described, for example, in U.S. Pat. No. 4,888,021.

To attach such a prosthetic patella surface to the patella, a portion of the patella must be cut away and a surface prepared to receive the prosthesis. Various surgical apparatus and devices have been proposed to accurately and replicably assist in this operation. For example, a patella planer is described by Smith & Nephew Richards, Inc. in connection with their Genesis (tm) Total Knee System. Another type of planer has been described and sold by Biomet, Inc. in connection with their AGC (tm) Total Knee System. Similarly, an apparatus has also been provided by Dow Corning Wright Company for use with the Whiteside Ortholoc (tm) Modular Knee System. Johnson & Johnson has sold a device for preparing the patella in connection with the PFC (tm) Knee System.

In general, however, although a planer is employed with each of these systems, the planer has generally been used to finish the surface of the patella. A preliminary resection with a sagittal saw has been necessary to prepare the patella before planing. In many cases this has been necessary because of the variation in physiologic thickness of a patella from patient to patient.

With a foregoing in mind, we have invented a patella planer which can be used in a single operation to produce a resected surface on a patella, suitable for receiving an artificial prosthetic patella.

It has been a further object of our invention to provide a patella planer which could accommodate patellas of varying thickness.

Another important object of our invention has been to provide a patella planer which would stop cutting at a desired depth of cut, irrespective of the initial thickness of the patella.

These and other features are advantages of our invention will be apparent from the following description taken with reference to the accompanying drawings.

SUMMARY OF OUR INVENTION

We have invented a patella planer which permits a resected surface to be prepared on a patella in a single operation. In connection with the patella planer, we have provided an adjustable stop which can be used on either side of the planer so that the planer may be used on the right or left knee. The adjustable stop has a floating zero pointer which can be set to accommodate varying thickness of the patient's patella. The amount of patella material to be removed can be selected by adjusting an offset stop pin.

DETAILED DESCRIPTION OF OUR PREFERRED EMBODIMENT

We will now describe our preferred embodiment of our invention with reference to the accompanying drawings. Like numerals will designate like parts throughout.

Figure 1:
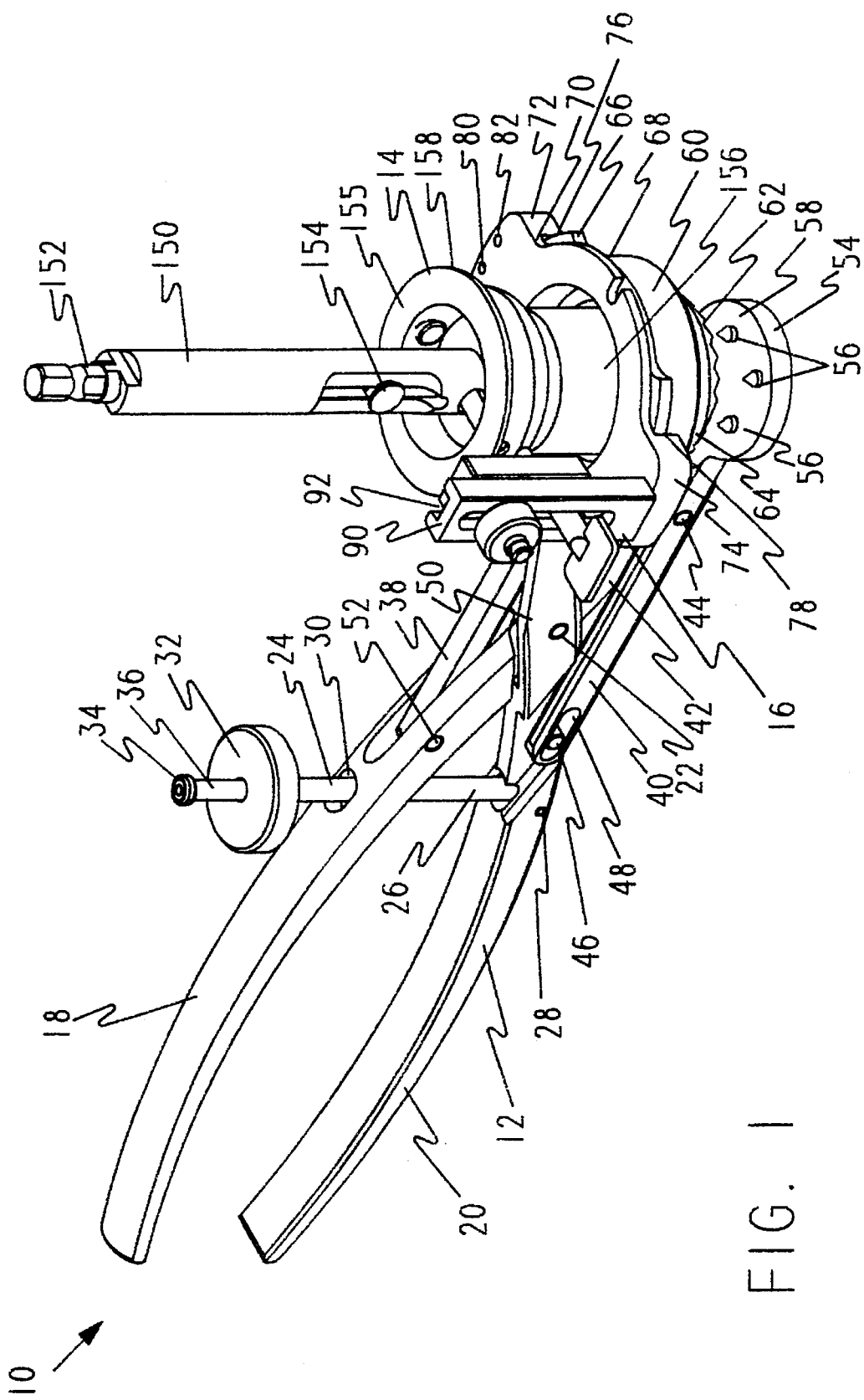
FIG. 1 is a prospective view of a patella planer according to our invention.
Figure 2:
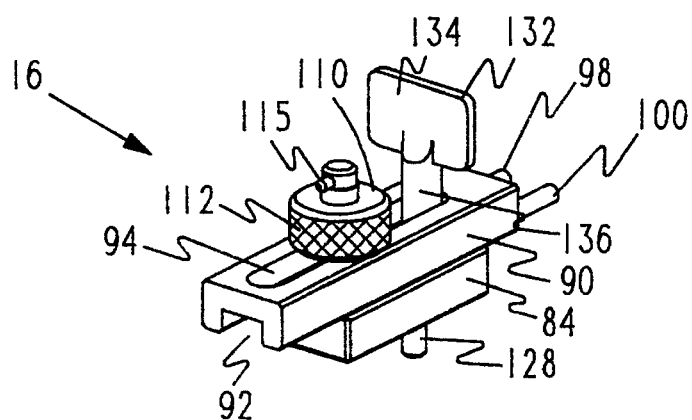
FIG. 2 is a prospective view of an adjustable stop for use with the planer of FIG. 1.

FIG. 1 illustrates a perspective view of a patella planer, generally designated 10, according to our invention. The planer 10 comprises a parallel jaw clamp 12 which is adapted to support the patient's patella and to guide a cutter 14. When connected to a source of torsional power, the cutter 14 can plane away a portion of the patella. A suitable cutter is available from Othy Inc. of Warsaw, Ind. The depth of cut of the cutter 14 into the patella is controlled by a planer stop 16. The planer stop 16 can be adjusted to accommodate any patella thickness and to provide one or more selected depths of cut, as will be more particularly described hereafter.

The parallel jaw clamp 12 comprises two handles 18, 20 pivotally joined at a central pin 22. A threaded rod 24 connects the lower handle 20 to the upper handle 18. A distal end 26 of the rod 24 is pinned with a press fit pin 28 to the lower handle 20. The rod 24 passes through a slot 30 in the upper handle. A lock nut 32 on the threaded rod tightens against the upper handle 18 to hold parallel jaw clamp 12 in a desired position against the patella. A rim 34, press fit on a proximal end 36 of the threaded rod 24, prevents the lock nut 32 from being inadvertently removed from the threaded rod. Attached to the handles 18, 20 are upper and lower arms 38, 40 respectively. As can best be seen in connection with the lower arm 40, the arms 38, 40 are connected to the handles so that they will close in the parallel faction. For example, the lower arm 40 is connected to a distal end 42 of the upper handle 18 by a pivoting pin 44. The lower arm 40 is also connected to the lower handle 20 by a pin 46 which rides in a slot 48 in the arm 40. The upper arm 38 is similarly connected to a distal end 50 of the lower handle 20 and to the upper handle 18 by a pin 52.

The lower arm 40 supports a base plate 54. The base plate has a plurality of spikes 56 on an upper side 58 thereof. When the planer 10 is used, the patient's patella is laid with an anterior side (that is, the side of the patella which does not articulate against the femur and tibia) against the spikes 56 on the base plate 54. Above the base plate 54 is a guide ring 60 which is connected to the upper arm 38. The guide ring 60 is essentially an annular body having circumferential teeth 62 on a lower edge 64 thereof. The teeth 62 press against the posterior side of the patella, that is, against the side which articulates against the femur and tibia. The cutter 14 passes through the guide ring 60 to act against the posterior side of the patient's patella. The guide ring 60 has a lip 66 at an upper edge 68. A removable support ring 70 rides on the lip 66. The support ring 70 has a right platform 72 and a left platform 74 on opposite sides of the support ring 70. The platforms 72,74 have bayonet locks 76,78 respectively so that the support ring 70 can be securely attached to the lip 66. In each platform, for example platform 72, two bores 80, 82 are provided for the attachment of the planer stop 16, as will be more particularly described below.

The planer stop 16 is shown most clearly in FIGS. 2 through 6. The planer stop 16 comprises a housing 84 having a longitudinal tongue 86 on an upper side 88 thereof. A support bar 90 has a longitudinal groove 92 which fits over the tongue 86. The support bar 90 also has a longitudinal slot 94 which exposes a top surface 96 of the tongue 86. Two mounting pins 98, 100, fixed to a distal end 102 of the support bar 90, fit into the bores 82 on the platform of the support ring 70. The planer stop 16 can, therefore, be placed on either the right or the left platform as needed to accommodate the particular situation confronting the surgeon. Two bores 104, 106 are provided in the tongue 86 of the housing 84. In the first bore 104, a partially threaded shaft 108 is press fit. Proximal threads 110 pass through the slot 94 in the support bar 90 and receive a thumb nut 112. The thumb nut 112 is retained on the partially threaded shaft 108 by a transverse pin 115. Tightening the thumb nut 112 against the support bar 90 locks the housing 84 in a selected position along the support bar. In the second bore 106, a floating zero pointer 114 is press fit. The function of this pointer will be more particularly explained hereafter.

Figure 3:
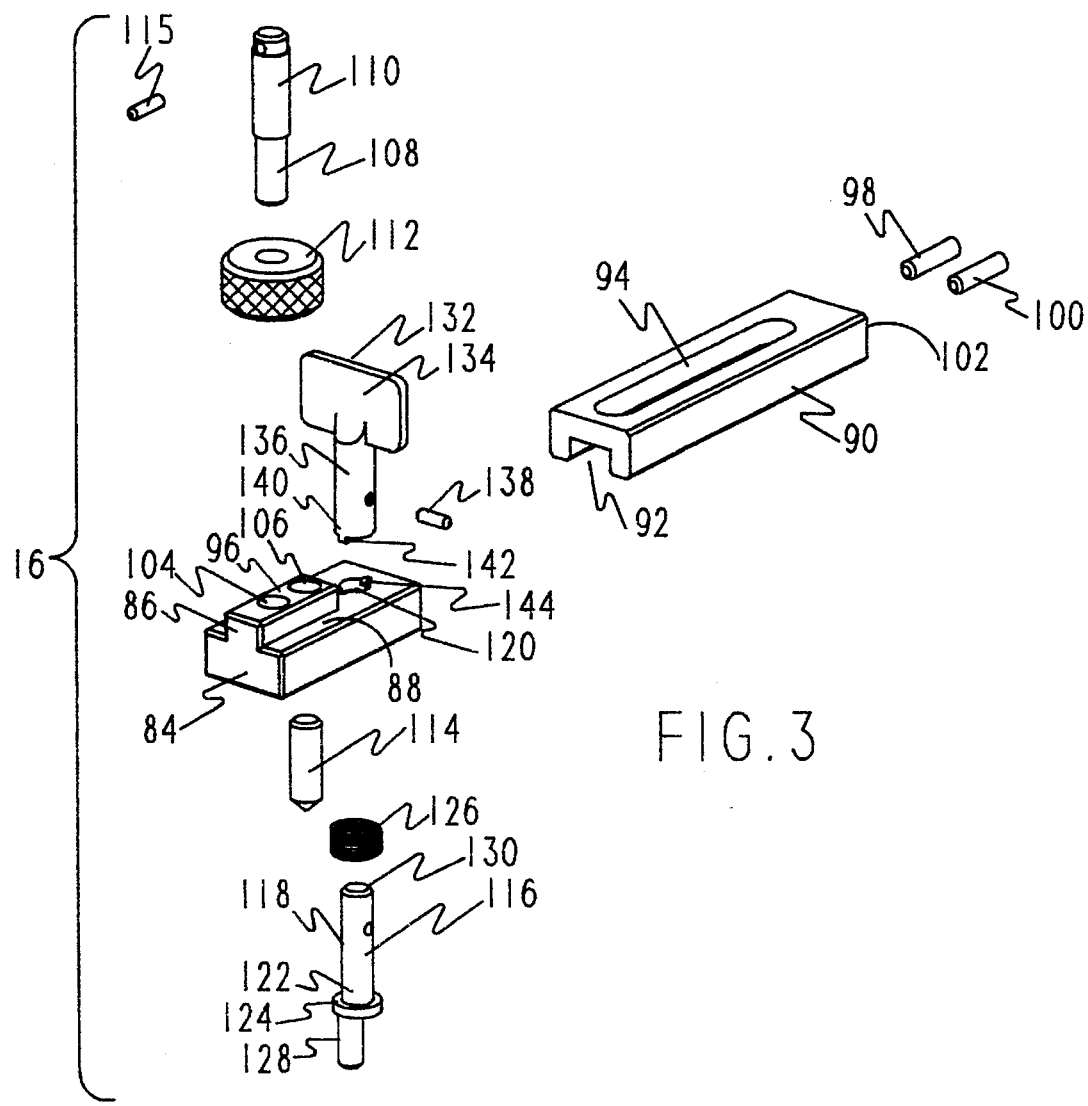
FIG. 3 is an exploded prospective view of the adjustable stop of FIG. 2.
Figure 4:
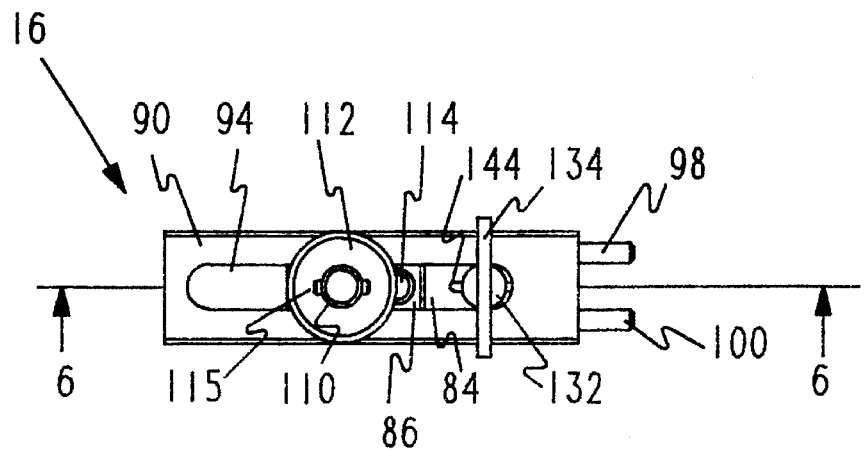
FIG. 4 is a top plan view of the adjustable stop of FIG. 2.
Figure 5:
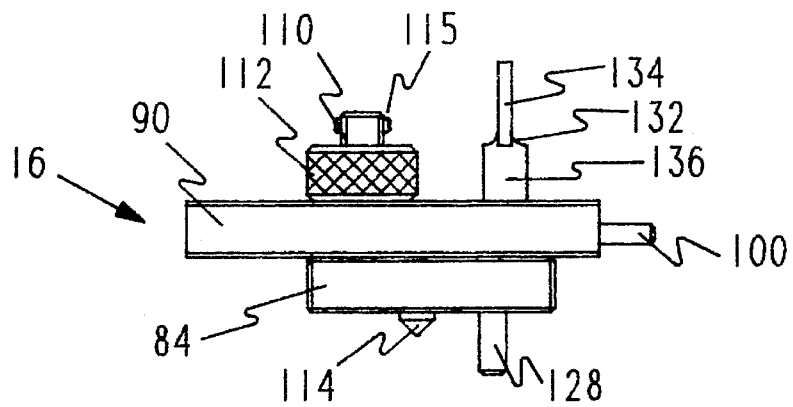
FIG. 5 is a side plan view of the adjustable stop of FIG. 2.
Figure 6:
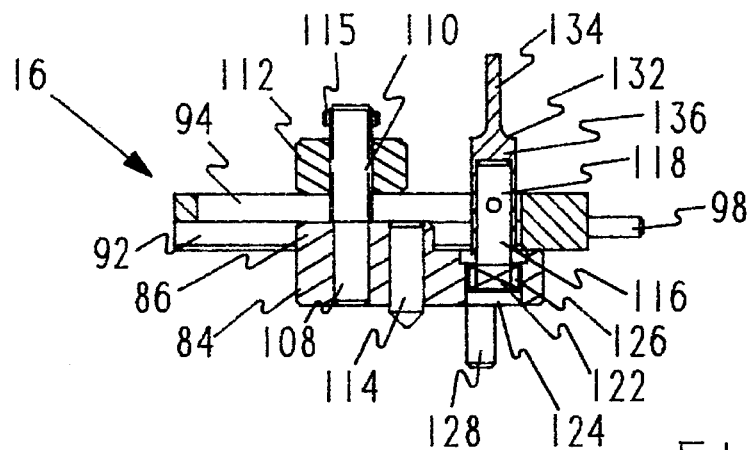
FIG. 6 is a through section of the adjustable stop taken along line 6—6 of FIG. 4.

The housing 84 also supports an offset stop pin 116. The stop pin 116 has a shaft 118 which passes loosely through a bore 120 in the housing 84. The shaft 118 also passes through the slot 94 in the support bar 90. At a distal end 122 of the shaft 118 there is a bearing surface 124 which supports a compression spring 126 within the housing 84. Attached to the bearing 124 is a stop shaft 128. As can be seen in FIG. 3 or FIG. 6, the shaft 118 defines a longitudinal axis and the stop shaft 128 defines a second longitudinal axis. These two axes are parallel to one another but are offset eccentrically.

At a proximal end 130 of the shaft 118, a handle 132 is attached to the stop pin 116. The handle 132 has a grip 134 and a hollow shaft 136 which fits over the shaft 118. A pin 138 connects the handle 132 to the shaft 118. At a distal end 140 of the hollow shaft 136, one or more index tabs 142 may be provided. These tabs 142 fit into index recesses 144 in the housing 84. The spring 126 normally urges the handle 132 against the housing 84, thus pressing the index tabs 142 into the index recesses 144. By pulling on the handle 132, the index tabs 142 can be disengaged from their associated recess 144 and the stop pin 116 can be rotated. This rotation selects the position of the stop shaft 128 with respect to the floating zero pointer 114.

As mentioned above, the cutter 14 is a commercially available surgical cutter or planer. Conventionally, such cutters 14 have a drive shaft 150 with a connection 152 proximally for attachment to as source of torsional power. A latch 154 connects a planer housing 155 to the drive shaft 150. The planer housing 155 has a cylindrical cup 156 which has cutting elements (not shown) oriented to abut the patella. Bone chips are scraped off the patella by the rotary motion of the cutter 14 and are captured within the cup 156. Proximally the planer housing 155 has a circumferential flange 158. In our preferred embodiment, this flange 158 is utilized both to adjust the position of the housing 84 and to engage the stop shaft 128 on the offset stop pin 116, preventing further cutting into the patella.

Figure 7:
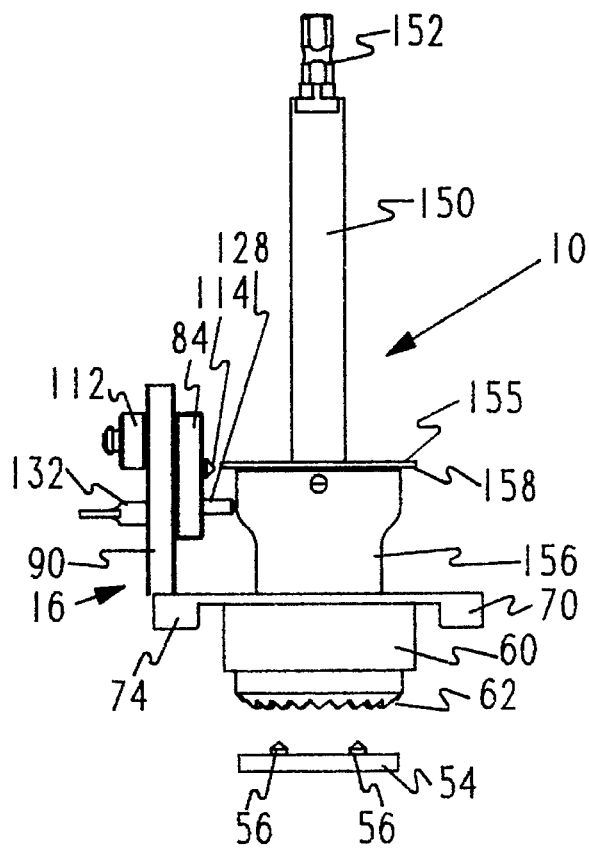
FIG. 7 is a front plan view of the patella planer.
Figure 8:
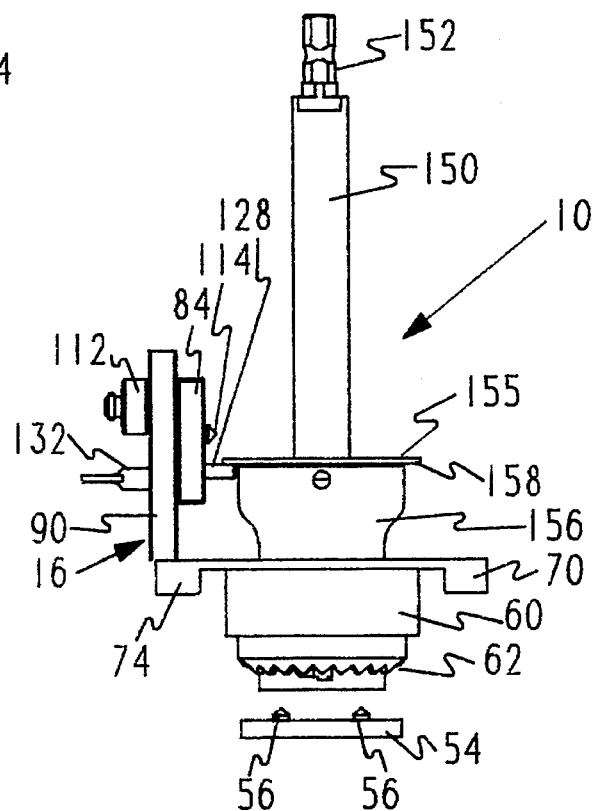
FIG. 8 is also a front plan view of the patella planer.

To use our invention, the patella of the patient is placed on the base plate 54. The guide ring 60 is then lowered against the posterior side of the patella and the handles 18, 20 are locked with the lock nut 32. The support ring 70 is placed on the guide ring 60. The cutter 14 is placed into the guide ring 60 and advanced until it rests against the posterior side of the patella. The planer stop 16 is then placed on the selected platform 74. The housing 84 is moved along the support bar 90 until the floating zero pointer 114 aligns with the flange 158 on the cutter 14, as illustrated in FIG. 7. The thumb nut 112 is then tightened to secure the housing 84 in its selected location. The offset pin 116 is then rotated to a selected position to select the depth of cut. In the preferred embodiment here illustrated, two positions are shown. With the stop shaft 128 oriented proximally away from the patella, a depth of cut of about seven millimeters would be selected. With the stop pin 116 rotated 180 degrees, the stop shaft 128 would be closer to the patella and the depth of cut would be approximately ten millimeters. Once the depth of cut has been selected, the cutter 14 can be driven to plane away a surface on the patella until the flange 158 contacts the stop 128, as illustrated in FIG. 8.

Our invention may be embodied in other specific forms without departing from the essential characteristics thereof. The foregoing description, therefore, is to be reviewed in all respects as illustrative and not restrictive, the scope of our invention being defined by the appended claims.

We claim as our invention:

1. A surgical apparatus for preparing a surface on a patella of a patient to receive a prosthetic implant, said apparatus comprising:

a circularly driven surface planer, a base plate for supporting said patella, guide means connected to said base plate for guiding said surface planer against said patella to cut away a portion of said patella, and stop means connected to said guide means for limiting said portion of said patella to be cut away by said surface planer, said stop means having means for selecting a depth of cut into said patella, and an adjustable pointer for setting said means for selecting a depth of cut to an initial zero condition dependant on the thickness of said patella.

2. The surgical apparatus according to claim 1 further comprising a clamp having upper and lower jaws which remain parallel to each other when said clamp is closed or opened, said base plate being attached to said lower jaw and said guide means being attached to said upper jaw.

3. The surgical apparatus according to claim 1 wherein said means for selecting a depth of cut further comprises means for selecting at least two depths of cut.

4. The surgical apparatus according to claim 3 wherein said means for selecting comprise a stop shaft eccentrically mounted with respect to an axis, said means for selecting being rotatable about said axis to select a position of said stop shaft, thereby controlling the depth of cut of said surface planer.

5. The surgical apparatus according to claim 4 further comprising a clamp having upper and lower jaws which remain parallel to each other when said clamp is closed or opened, said base plate being attached to said lower jaw and said guide means being attached to said upper jaw.

6. The surgical apparatus according to claim 1 wherein said adjustable pointer further comprises a housing supporting a pointer and said means for selecting said depth of cut, support means connected to said guide means, said housing being slidingly connected to said support means, and means for selectively securing said housing at a selected location along said support means.

7. The surgical apparatus according to claim 6 further comprising a clamp having upper and lower jaws which remain parallel to each other when said clamp is closed or opened, said base plate being attached to said lower jaw and said guide means being attached to said upper jaw.

8. The surgical apparatus according to claim 6 wherein said means for selecting a depth of cut further comprises means for selecting at least two depths of cut.

9. The surgical apparatus according to claim 8 wherein said means for selecting comprise a stop shaft eccentrically mounted with respect to an axis, said means for selecting being rotatable about said axis to select a position of said stop shaft, thereby controlling the depth of cut of said surface planer.

10. The surgical apparatus according to claim 6 wherein said guide means further comprises means for attaching said support means at a selected one of at least two locations on said guide means.

11. The surgical apparatus according to claim 10 further comprising a clamp having upper and lower jaws which remain parallel to each other when said clamp is closed or opened, said base plate being attached to said lower jaw and said guide means being attached to said upper jaw.

12. The surgical apparatus according to claim 10 wherein said means for selecting a depth of cut further comprises means for selecting at least two depths of cut.

13. The surgical apparatus according to claim 12 wherein said means for selecting comprise a stop shaft eccentrically mounted with respect to an axis, said means for selecting being rotatable about said axis to select a position of said stop shaft, thereby controlling the depth of cut of said surface planer.

14. The surgical apparatus according to claim 13 further comprising a clamp having upper and lower jaws which remain parallel to each other when said clamp is closed or opened, said base plate being attached to said lower jaw and said guide means being attached to said upper jaw.

* * * * *